United States Patent [19]

Chagnon et al.

[11] Patent Number: 5,382,468
[45] Date of Patent: Jan. 17, 1995

[54] BIODEGRADABLE MAGNETIC MICROCLUSTERS AND METHODS FOR MAKING THEM

[75] Inventors: Mark S. Chagnon, Pelham, N.H.; John R. Ferris, Newburyport, Mass.; Barry L. Fiore, Auburn, Ala.; Michelle J. Carter, Derry; Tracy J. Hamilton, Hudson, both of N.H.

[73] Assignee: Molecular Bioquest, Inc., Atkinson, N.H.

[21] Appl. No.: 995,070

[22] Filed: Dec. 22, 1992

Related U.S. Application Data

[62] Division of Ser. No. 806,478, Dec. 13, 1991, Pat. No. 5,225,282.

[51] Int. Cl.$^6$ ............................................. B32B 27/02
[52] U.S. Cl. ................................... 428/328; 428/332; 428/402.24; 428/407; 428/900; 436/173
[58] Field of Search ................... 428/407, 402.24, 328, 428/332, 900; 252/62.54, 62.58, 62.64; 436/526, 173

[56] References Cited

U.S. PATENT DOCUMENTS

| | | | |
|---|---|---|---|
| 4,454,234 | 6/1984 | Czerlinski | 436/526 |
| 4,675,173 | 6/1987 | Widder | 424/9 |
| 4,795,698 | 1/1989 | Owen et al. | 435/4 |
| 5,147,573 | 9/1992 | Chagnon | 252/62.52 |
| 5,213,788 | 5/1993 | Ranney | 424/9 |

FOREIGN PATENT DOCUMENTS

| | | | |
|---|---|---|---|
| WO8702063 | 4/1987 | WIPO | C12Q 1/00 |
| WO9109678 | 7/1991 | WIPO | B03C 1/00 |
| WO9115243 | 10/1991 | WIPO | A61K 49/00 |
| WO9202940 | 2/1992 | WIPO | H01F 1/00 |
| WO9204916 | 4/1992 | WIPO | A61K 47/48 |

OTHER PUBLICATIONS

J. Appl. Phys. vol. 41, No. 3, Mar. 1970, pp. 1064–1072 R. Kaiser et al "Magnetic Properties of Stable Dispersions of Subdomain Magnetite Particles".

Invest Radiol. vol. 27, No. 6, Jun. 1992, pp. 450–455 A. Iannone "Detection and Quantification in Rat Tissues of Magnetite as Demonstrated by Electron Spin Resonance Spectroscopy".

*Primary Examiner*—Stevan A. Resan
*Attorney, Agent, or Firm*—Hayes, Soloway, Hennessey, Grossman & Hage

[57] ABSTRACT

Subdomain metal or metal oxide particles covalently coupled to chemically reactive organic moieties and subsequently reacted together to form biodegradable magnetic microclusters are disclosed. The magnetic microcluster can be used as contrast agents in NMR imaging for the production of images suitable for use in diagnosis, for in vivo delivery and targeting of drugs, as in vivo, biodegradable agents for the sequestering of free metal ions in the treatment of metal driven disease.

3 Claims, No Drawings

BIODEGRADABLE MAGNETIC MICROCLUSTERS AND METHODS FOR MAKING THEM

This is a divisional of copending application Ser. No. 07/806,478 filed on Dec. 13, 1991, now U.S. Pat. No. 5,225,282.

BACKGROUND OF THE INVENTION

NMR has found increasing use since the early 1970's as a medical diagnostic tool, in particular as an imaging technique. The technique provides high resolution and differentiation of soft tissue without the use of potentially harmful radiation. For several years, radiologists believed that with the high contrast achieved in NMR imaging in soft tissues without the use of contrast agents, the use of contrast agents would not be necessary. However, it has recently been found that paramagnetic complexes can be used with advantage to achieve enhanced contrast in NMR imaging thereby extending the diagnostic utility of the technique.

The nuclei of many atoms have a property called spin which is associated with a small magnetic moment. In the absence of an external magnetic field, the distribution of the orientations of the magnetic moments is random. In the presence of a static magnetic filed the nuclear magnetic moments process about the field direction and there will be a net alignment in the field.

In NMR imaging, a patient is placed in a static field and a short radio frequency pulse is applied via a coil surrounding the patient. The radio frequency or RF signal is selected for the specific nuclei which are to be resonated. The RF pulse causes the magnetic moments of the nuclei to align with the new field and to process in phase, and on termination of the pulse moments return to the original distribution of alignments with respect to the static field and to a random distribution of procession phases giving off a nuclear magnetic resonance signal which can be picked up by a receiving coil. The NMR signal is generally from $^1H$ nuclei and represents a proton density of the tissue being studied. R. S. First, *NMR In Medicine In The 1980's* (1983).

Two additional values can be determined when the RF pulse is turned off and the nuclear magnetic moments are relaxing or returning to equilibrium orientations and phases. These are T1 and T2, the spin-lattice and spin-spin relaxation times. T1 represents a time characteristic of the return to equilibrium spin distribution, i.e. equilibrium alignment of the nuclear magnetic moments in the static field. T2 on the other hand represents a time characteristic of the return to random precession phase distribution of the nuclear magnetic moments.

The NMR signal that is generated thus contains information on proton density, T1 and T2 and the images that are generated are generally the result of complex computer data reconstruction on the basis of that information.

The potential application of contrast agents in extending the diagnostic utility of NMR imaging is discussed, for example, by R. C. Brasch in *Radiology* 147:781 (1983). Although numerous methods of contrast are available, many, such as manipulation of tissue temperature, viscosity or hydration, are clearly not clinically feasible and the most advantageous prior art technique appears to be the use of paramagnetic contrast agents to reduce the spin-lattice relaxation of time T1.

A paramagnetic substance is one which contains one or more fundamental particles (electrons, protons or neutrons) with a spin whose effect is not cancelled out by another particle with like spin. These particles create a small magnetic field which can interact with neighboring nuclear magnetic dipoles to cause a reorientation of the dipole, i.e. a change in nuclear spin and precession phase.

Since the magnetic field created by an electron is much greater than that created by a proton or a neutron, in practice only ions, molecules, radicals or complexes, which are paramagnetic due to the presence of one or more unpaired electrons, are used as paramagnetic NMR contrast agents.

The contrast effect of paramagnetic ions and complexes is predominantly the result of reduction in T1. However, paramagnetic stable free radicals will also cause some reduction in T2. R. C. Brasch, *Radiology*, 147:781 (1983). Nevertheless the relative reduction of T1 is greater than that of T2.

The use of paramagnetic contrast agents in NMR imaging has been extensively investigated and solutions and colloidal dispersions of such agents have been proposed for oral and paraenteral administration in conjunction with diagnostic imaging.

Ferromagnetic materials have also been used as contrast agents because of their ability to decrease T2. Medonca-Dias and Lauterbur, *Magn. Res. Med.*, 3:328 (1986); Olsson et al, *Mag. Res. Imaging*, 4:437 (1986). Ferromagnetic materials have high, positive magnetic susceptibilities and maintain their magnetism in the absence of an applied field. The use of ferromagnetic materials as MRI contrast agents are described, for example, in PCT Application No. WO86/01112 and PCT Application No. WO85/043301.

A third class of magnetic materials, termed superparamagnetic materials, have been used as contrast agents. Saini et al., *Radiology*, 167:211 (1987); Hahn et al., *Soc. Mag Res. Med.* 4(22):1537 (1986). Like paramagnetic materials, superparamagnetic materials are characterized by an inability to remain magnetic in the absence of an applied magnetic field. Superparamagnetic materials can have magnetic susceptibilities nearly as high as ferromagnetic materials and far higher than paramagnetic materials. Bean and Livingston, *J. Appl. Phys., Supp.* 1 to Vol. 30, 1205, (1959).

Ferromagnetism and superparamagnetism are properties of lattices rather than ions or gases. Iron oxides such as magnetite and gamma ferric oxide exhibit ferromagnetism or superparamagnetism depending on the size of the crystals comprising the material, with larger crystals being ferromagnetic. G. Bate *In: Ferromagnetic Materials*, Vol. 2, Wohlfarth (ed.) p. 439.

As generally used, superparamagnetic and ferromagnetic materials alter the MR image by decreasing T2 resulting in image darkening. When injected, crystals of these magnetic materials accumulate in the targeted organs or tissues and darken the organs or tissues where they have accumulated.

Superparamagnetic particles have also been shown to be effective for the delivery and targeting of drugs directly to an infected organ, tissue or joint. Delivery systems, for example, using magnetic particles 100 Angstroms (A) in diameter encapsulated in albumin microspheres have been demonstrated for delivery of chemotherapeutic agents into Yoshida rat sarcoma. Widder, U.S. Pat. No. 4,345,588 (1982); Senyei et al., U.S. Pat. No. 4,357,259 (1982).

All of the aforementioned in vivo applications have the marked disadvantage of the lack of particle or cluster biodegradability. Half lives of $Fe_3O_4$ 100 A particles, for example, are in excess of 8 months when injected into a patient's body.

Particles of less than 50 A in diameter will generally clear from a patient after in vivo application very quickly; however, below 50 A in diameter there is no evidence of domain wall support and particles of this size are non-magnetic.

SUMMARY OF THE INVENTION

The present invention relates to biodegradable superparamagnetic microclusters and methods of their preparation. The present microclusters comprise clusters of metal or metal oxide particles that are about 70 A or less in crystallite size and which are non-magnetic in the unclustered state. The non-magnetic unit crystals ("crystallites") are encapsulated or bonded together to form a superparamagnetic cluster of crystallites having a cluster size of from about 100 A to 2 microns in diameter.

In one embodiment of the present invention, the individual non-magnetic crystallites are coated with monomers functionalized to participate in subsequent crosslinking reactions. Accordingly, the monomers are adsorbed or covalently bound to the crystallites, and the crystallites are covalently linked by crosslinking between the coated crystallites, thereby forming magnetic microclusters. For physiological applications, the cross-links are hydrolyzable bonds which hydrolyze in the physiological environment. In another embodiment, the crystallites can be coated directly with polymer coatings, which encapsulate the crystallites into magnetic microclusters, wherein the microcluster is conveniently degraded by simply dissolving it in a solvent suitable for the given polymer.

The magnetic clusters are biodegradable to the unit crystallites and become non-magnetic upon biodegradation. The magnetically responsive microclusters of this invention overcome problems associated with size, surface area, biodegradation, and magnetic character of previously developed magnetic particles. The present microclusters are useful in clinical applications, such as contrast agents for nuclear magnetic resonance imaging.

DETAILED DESCRIPTION OF THE INVENTION

The present invention is based on the discovery that, remarkably, when a population of non-magnetic particles of iron metal, magnetic iron oxide or magnetic metal alloy having a diameter of about 70 A or less are linked or encapsulated into a bead structure of about 100 A or greater in diameter, the bead will behave as a superparamagnetic species. If the bead is designed with appropriate chemistry rendering the bead biodegradable, the magnetizable particle will, upon degradation to the unit crystal size, become non-magnetic.

The present magnetic microclusters are clusters of particles comprising a core of metal, metal alloy or metal oxide. These 70 A or less particles are referred to herein as "crystallites". The individual crystallites can be coated with a functionalized organo-metallic monomer which is adsorbed onto or covalently bound to the crystallites thereby forming an organometallic polymer coating. The functional or reactive terminal groups on the organometallic polymer coating are then reacted together via chemical reactions, e.g. covalent crosslinking, formation of coordination complexes or bioaffinity coupling to form magnetizable microclusters. These magnetizable clusters have a mean cluster size of about 100 A to about 2 microns in diameter and are referred to hereinafter as "microclusters".

Each crystallite is a subdomain (less than 70 A) crystal, or group of crystals, of a transition metal, alloy or metal oxides comprised of trivalent and divalent cations of the same or different transition metals or magnetic metal crystal group. Metals, alloys and oxides which are useful as magnetic core material in the present invention include the metals, alloys, and oxides based on metals which appear in the Periodic Table in Groups 4a and b, 5a and b, 6a and 7a. These include, for example, divalent transition metals, such as iron, magnesium, manganese, cobalt, nickel, zinc and copper, alloys of these metals such as iron alloys or oxides (e.g., iron magnesium oxide, iron manganese oxide, iron cobalt oxide, iron nickel oxide, iron zinc oxide and iron copper oxide), cobalt ferrite, samarium cobalt, barium ferrite, and aluminum-nickel-cobalt and metal oxides including magnetite ($Fe_3O_4$), hematite ($Fe_2O_3$) and chromium dioxide ($CrO_2$). By way of illustration, the crystallite may be comprised of crystals of iron or iron oxide, or may consist of a single crystal of an iron oxide or metal alloy.

The present crystallites are preferably between about 0.001 and about 0.007 microns (10 A to 70 A) in diameter and have a surface area of about 25 to 1000 square meters per gram.

The crystallite particles can be prepared according to the following general procedure: metal salts, or organometallocenes, are precipitated in a base at high temperature and pressure to form fine magnetic metal oxide crystals. The crystals are redispersed, then washed in water and in an electrolyte. Magnetic separation can be used to collect the crystals between washes, as the crystals are generally superparamagnetic at this stage. The crystals are then milled, for example, in a ball mill, under conditions sufficient to form subdomain (less than 50 A) crystallites, which are non-magnetic.

In one embodiment of the present invention, superparamagnetic iron oxide particles are made by precipitation of divalent ($Fe^{2+}$) and trivalent ($Fe^{3+}$) iron salts, for example, $FeCl_2$ and $FeCl_3$, in base and then milled to produce the sub 50 A particles. The ratio of $Fe^{2+}$ and $Fe^{3+}$ can be varied without substantial changes in the final product by increasing the amount of $Fe^{2+}$ while maintaining a constant molar amount of iron. A $Fe^{2+}/Fe^{3+}$ ratio of about 2:1 to about 4:1 is useful in the present invention; a ratio of about 2:1 $Fe^{2+}:Fe^{3+}$ is particularly useful. An $Fe^{2+}:Fe^{3+}$ ratio of 1:1 produces magnetic particles of slightly inferior quality to those resulting from the higher $Fe^{2+}/Fe^{3+}$ ratios, the particle size is more heterogeneous than that resulting from $Fe^{3+}Fe^{2+}$ of 2:1 or 4:1.

In this embodiment, aqueous solutions of the iron salts are mixed in a base, such as ammonium hydroxide, which results in the formation of a crystalline precipitate of superparamagnetic iron oxide. The precipitate is washed repeatedly with water by magnetically separating and redispersing it until a neutral pH is reached. The precipitate is then washed once in an electrolytic solution, e.g. a sodium chloride solution. The electrolyte step is important to insure fineness of the iron oxide crystals. The precipitate is then washed with a solvent (e.g. acetone) to remove all of the water.

The metal powder is then collected, e.g. by magnetic separation or by filtration, and added to a commercial ball mill as an acetone slurry in a concentration of about 1–25%. The mill is filled about halfway with ¼" stainless steel balls and the slurry is milled for a period of time necessary to form the subdomain crystallites, generally about 3–60 days. At the completion of the milling period, the subdomain particle slurry formed is treated as the magnetite described in the previous section.

In another embodiment of the present invention, the crystallites can be made by precipitating metal powders using borohydrides and reducing the particle size by milling the resulting precipitate, for example, in a ball mill. In this process, the metal powder is precipitated from an aqueous solution of, for example, $Fe^{+2}$ or $Fe^{+3}$ salt, with sodium borohydride. The resulting properties of the metal powder are unaffected by the balance of the counter ion or by the iron metal salt selected. Complete precipitation occurs spontaneously upon addition of the borohydride. The magnetic metal powder is then collected by magnetic separation or filtration, washed with water to remove all soluble salts, and then washed in acetone to remove all residual water. The particle is added as an aqueous slurry in a concentration of about 1–25% by weight to a commercial ball mill filled half way with ¼" stainless steel balls and milled for about 10–60 days. At the completion of the milling period, a subdomain metal slurry is formed.

In yet another embodiment of this invention, subdomain crystallites are grown directly from solution at high temperature and pressure. For example, an aqueous solution of 2:1 $Fe^{+2}/Fe^{+3}$ is added to an aqueous solution of ammonium hydroxide at >60° C. and >1 atmosphere of pressure. The pressure and temperature are slowly reduced to begin formation of a crystal seed bead. The reactants are incubated at the lower temperature and pressure until the precipitation is complete and the reagents are completely used. The pressure and temperature of the reaction vessel are then reduced to ambient conditions and the particles are collected by filtration, washed 3 times, e.g., with deionized water, to remove excess reactants and 3 times with a solvent, such as acetone, to remove excess water. The subdomain particles thus prepared are non-magnetic.

In another embodiment of this invention, the subdomain crystals are grown by the reaction of a metallocene with a base. In one embodiment of this method, ferrocene is combined with iron II hydroxide. Iron II hydroxide is prepared by reacting an aqueous solution on iron II (ferrous) chloride, for example, with ammonium hydroxide to form a gelatinous precipitate of iron II hydroxide ((FeO(OH)). The iron hydroxide is collected by filtration, transferred into a commercial ball mill filed halfway with ¼" stainless balls and one-quarter way with water, and the resulting iron hydroxide slurry is milled for a period of 1–30 days.

A second ball mill is one-quarter filled with an aqueous slurry of ferrocene (1–25%) and half filled with ¼" stainless balls. The ferrocene slurry is milled for a period of 1–90 days to produce ferrocene crystals in the size range desired for the finished iron oxide crystallites.

The contents of the two ball mills are then mixed together and milling is continued for about 1 hour to about 10 days to produce the subdomain crystallites. This method is described in detail in co-pending U.S. application Ser. No. 07/565,801 filed Aug. 10, 1990, by M. S. Chagnon et al, the teachings of which are hereby incorporated herein by reference.

Other divalent transition metal salts such as magnesium, manganese, cobalt, nickel, zinc and copper salts may be substituted for iron salts in the precipitation and milling procedure to yield magnetic metal oxides. For example, the substitution of divalent cobalt chloride ($CoCl_2$) for $FeCl_2$ in the above procedure produced ferromagnetic metal oxide particles. Ferromagnetic metal oxide particles such as those produced with $CoCl_2$ can be washed in the absence of magnetic fields by employing conventional techniques of centrifugation or filtration between washings to avoid magnetizing the particles.

The crystallites can be coated with an organo-metallic monomer material capable of adsorptive or covalently bonding to the magnetic core particles. The organo-metallic monomers also contain an aliphatic moiety and organic functionality to which a wide variety of organic and/or biological molecules can be coupled. Organo-metallic monomers useful for the present coated particles are organic coordinate complexes of selected transition and/or post transition metals which are capable of forming a stable coordination compound which can be adsorbed onto or covalently bound to the magnetic particle. The organometallic monomers must be capable of crosslinking in situ on the particle surface, thereby forming the organo-metallic polymer coating.

Particularly useful organo-metallic compounds are coordinate complexes formed from selected transition metals (e.g., Fe, Ni, Co, Cr, Ti, Zr, Hf, V, Ta, Nb) and/or post-transition metals (e.g. Sn, Sb). Organo-titanium compounds which are useful include, for example, titanium-tetra-isopropoxide, amino-hexyl-titanium-tri-isopropoxide, amino-propyl-titanium-tri-isopropoxide and carboxyl-hexyl-titanium-tri-isopropoxide. Other compounds which are useful include silicon-tetra-isopropoxide and carbon-tetra-isopropoxide. The monomers must be able to be functionalized in a manner that allows the polymer coating formed therefrom to form covalent bonds with bioaffinity or chemical reactants. For this purpose, the monomers can be post-functionalized or derivatized, if necessary, with an aliphatic "spacer arm" which is terminated with an organic functional group capable of coupling with bioaffinity adsorbents or chemically reacting to form covalent cross linkages or forming coordinate complexes. The "spacer arm" is an aliphatic hydrocarbon having from about 3 to about 30 atoms, e.g. carbon, nitrogen and/or oxygen atoms. The purpose of the spacer arm is to provide a non-reactive linker (or spacer) between the organic functional group and the polymer coating. The organic functional group is generally a reactive group such as an amine ($NH_2$), carboxy group (COOH), cyanate (CN), phosphate ($PO_3H$), sulfate ($SO_3H$), thiol (SH), or hydroxyl (OH) group, or a functional ligand such as a catechin.

In one embodiment of the present invention, amino-hexyl-titanium-tri-isoproxide is coated onto the magnetic particle of choice, and thermally crosslinked to form an organo-titanium polymer coating having an aliphatic spacer arm (the hexyl moiety) and organic functional group.

In one embodiment of the present method, an organo-titanium compound, such as titanium-tetra-isopropoxide which lacks the spacer arm and organic functional group, is functionalized by reaction with an agent such as 1-hydroxy-6-amino hexane, to form the amino-hexyl-titanium-tri-isopropoxide. A method of coating metal or metal oxide particles with an organometallic coating is described in detail in co-pending U.S. application Ser. No. 07/566,169, filed Aug. 10, 1990, by M.S. Chagnon, the teachings of which are hereby incorporated herein by reference. The functionalized particle can then be reacted, coupled, or crosslinked via the reaction method of choice.

In a further embodiment of the present invention, the biodegradable magnetic microclusters can be formed by macromolecular encapsulation of the non-magnetic metal or metal oxide particles. More particularly, the particle crystallites are prepared as a particle slurry and are mixed with a solution of polymer for a time sufficient to substantially disperse the polymer within the slurry. The crystallites are then encapsulated by the addition of a solvent which causes the polymer to flocculate and collapse onto their surface. The encapsulated crystallites thereby form a superparamagnetic cluster having a cluster size of from about 100 A to 2 microns in diameter, with a saturation magnetization of about 2,000 gauss, with no remnant magnetization. Particularly useful polymers include poly(vinyl alcohol), hydroxypropyl cellulose, carboxymethylcellulose, poly(vinyl pyrrolidone), polyurethanepolyester block copolymers, polystyrene and poly(vinyl acetate)-poly(vinyl chloride) copolymers. These clusters can then be conveniently degraded, for example, by dissolving in a solvent suitable for a given polymer. At that point, the particles no longer remain encapsulated and the resulting unit crystals have no magnetization.

The microclusters formed by crosslinking or bonding between the non-magnetic crystallites, or by encapsulation of said crystallites, are superparamagnetic in character. These superparamagnetic microclusters can be used in a number of in vitro and/or in vivo applications where magnetic particles are used. For example, a bioaffinity adsorbent can be covalently linked to the organometallic coating, on the microcluster, and the microcluster can then be used in in vitro separations. Methods of covalently linking a bioaffinity adsorbent to an organometallic-coated particle are described in detail, for example, in co-pending U.S. application Ser. No. 07/566,169, filed Aug. 10, 1990 by M. S. Chagnon, the teachings of which are incorporated herein by reference.

The present microclusters because of their unique characteristics are particularly useful for in vivo and in vitro applications, specifically magnetic tracers for homogeneous immunoassays. The microclusters are superparamagnetic, that is, they are responsive to an applied magnetic field, but do not exhibit remnant magnetization once the magnetic field has been removed. The microclusters are biodegradable, and once the cluster has degraded into its component crystallites, the crystallites are non-magnetic. The microclusters are therefore well suited for use in in vivo diagnostic localization of cells or tissues recognized by the particular bioaffinity adsorbent coupled to the particle, and also for magnetically directed delivery of therapeutic agents coupled to the particles to pathological sites. The microclusters are particularly useful for use in magnetic resonance imaging.

The invention will now be further illustrated by the following examples.

EXAMPLES

Example 1: Preparation of Subdomain Magnetite Particles by Precipitation and Subsequent Size Reduction by Milling 200 grams (1.58 moles) of ferrous chloride (VWR Scientific) and 325 grams (2.0 moles) of ferric chloride were dissolved in 3 liters of water. 2000 grams of ammonium hydroxide (VWR Scientific) concentrate were added at a rate of 50 ml/minute under constant agitation, during which time the temperature of the solution was kept between 25 and 40 degrees C. After the addition of the ammonium hydroxide was complete, the magnetic particle ($Fe_3O_4$) aqueous slurry was allowed to cool to room temperature.

The particles were then washed with 5 volumes of water, and collected between each wash. On the final wash step the particles were adjusted to an aqueous slurry volume of 25% and added to a commercial ball mill. The mill was filled ½ way with ¼" stainless steel balls and the slurry was milled for a period of 60 days to reduce the particles to 30 A diameter.

Example 2: Preparation of Subdomain Metal Particles by Sodium Borohydride Reduction and Size Reduction by Milling 200 gm (1.58 moles) of ferrous chloride was dissolved in 1 liter of water. 500 gm of dry sodium borohydride were added to the solution to form a fine iron powder precipitate. The precipitate was washed with water and collected by filtration. The filtered powder was resuspended in water and re-filtered. The washing procedure was done 4 additional times. On the final suspension, the slurry was adjusted to a concentrate of 20% and milled as described in Example 1 for a period of 75 days to produce particles with a mean diameter of less than 50 A. The resulting particles had no magnetic field response.

Example 3: Preparation of Subdomain Magnetite Particles by Reaction of Particulate Ferrocene and Iron (II) Hydroxide A 100 gm slurry containing 20% by weight ferrocene in water was milled in a commercial ball mill as described in Examples 1 and 2 for 60 days.

A second slurry was prepared by the following procedure: An aqueous solution containing 20 gm of ferrous sulfate was precipitated using 50 gm of ammonium hydroxide concentrate to form the gelatinous ferrous hydroxide. The gel was filtered and the filtrate washed with 5–100 gm volumes of water. The washed gel was then made into a 20% aqueous slurry and milled as previously described for 30 days.

The ferrocene and hydroxide slurries were mixed and milled together for 3 days to form fine $Fe_3O_4$ crystallites. The crystallites had a mean diameter of 30 A and were non-responsive to a magnetic field.

Example 4: Preparation of Amino-Hexyl-Titanium-Tri-Isopropoxide 0.1 moles of titanium-tri-isopropoxide (Tyzor TPT Dupont, Wilmington, Del.) and 0.1 moles of 6-amino-1-hexanol were added to a 50 ml beaker and stirred at room temperature for 1 minute to form 0.1 mole of amino-hexyl-titanium-tri-isopropoxide. The reaction mixture was heated to 70° C. for 10 minutes to evaporate the isopropyl alcohol formed during the reaction.

The material was cooled to room temperature and used as a monomer in making the tetravalent titanium organometallic coating in Example 5.

Example 5: Preparation of Amine Functional Organo-titanate Coated Particle

Particles were prepared according to the procedures set out in Examples 1, 2 and 3. The particles were washed 5 times with water and 3 times with acetone to remove the water. N,N-dimethyl formamide (DMF) was added to the precipitate in the following ratio:10 ml of DMF per gram of particle. The mixture was loaded into an Eiger Mill and milled continuously for 10 minutes. The mixture was then transferred to a beaker and heated with stirring for 30 minutes at 100° C. The amine functional organo-titanate prepared in Example 4 was immediately added after preparation with constant stirring to the mixture in a ratio of 1 g dry $Fe_3O_4$ per 3 g of amine functional organo-titanate.

This mixture was then heated with stirring for 20 minutes at 65 degrees C. and then passed through the Eiger Mill for two passes. The resulting material was washed five times with water, the coated particles were collected by filtration and the aqueous waste was decanted.

Example 6: Preparation of Hydroxy-Hexyl-Titanium-Tri-Isopropoxide 0.1 moles of titanium-tri-isopropoxide (Tyzor TPT DuPont, Wilmington, Del.) and 0.1 moles of 6-hydroxy-1-hexanol were added to a 50 ml beaker and stirred at room temperature for 1 minute to form 0.1 mole of hydroxy-hexyl-titanium-tri-isopropoxide. The reaction mixture was heated to 70 degrees C. for 10 minutes to evaporate the isopropyl alcohol formed during the reaction.

The material was cooled to room temperature and used as a monomer in making the tetravalent titanium organometallic coating in Example 7.

Example 7: Preparation of Alcohol-Functional Organo-titanate Coated Particle Particles were prepared according to the procedures set out in Examples 1, 2 and 3. The particles were washed 5 times with water and 3 times with acetone. N,N-dimethyl formamide (DMF) was added to precipitate in the following ratio:10 ml of DMF per gram of particle. The mixture was loaded into an Eiger Mill and milled continuously for 10 minutes. The mixture was then transferred to a beaker and heated with stirring for 30 minutes at 100 degrees C. The alcohol functional organo-titanate prepared in Example 6 was immediately added after preparation with constant stirring to the mixture in a ratio of 1 g dry $Fe_3O_4$ per 3 g of amine functional organo-titanate.

This mixture was then heated with stirring for 20 minutes at 65 degrees C. and then passed through the Eiger Mill for two passes. The resulting material was washed five times with water, the coated particles were collected by filtration and the aqueous waste was decanted.

Example 8: Coated Particles of Dihydroxy-Benzene-Hexyl-Titanium-Tri-Isopropoxide 10 grams of amino functional particles prepared in Example 5 were prepared in an aqueous slurry containing 10% by weight particle. 10 grams of 2,3-dihydroxy-5-benzoic acid were added to the slurry and dissolved. 5 grams of cyclohexyl carbodiiomide were added to form a C6 amide coupled product with a 2,3 dihydroxy-benzene termination.

Example 9

An organo-titanium coated particle was prepared exactly as in Example 4 and 5 except that 6-carboxy-1-hexanol was used in place of 6-amino-1-hexanol to form a carboxy terminated organo-titanium coated particle.

Example 10: Formation of a Magnetic Cluster 10 grams of 2,3 dihydroxy-benzene terminated particles as prepared in Example 8, and 10 grams of carboxy terminated magnetic particles as prepared in Example 9 were mixed with 5 grams of sodium molybdate. The reaction mixture was stirred for a period of 24 hours. The resulting materials were molybdenum coordinate particle clusters about 1 micron in diameter that had a saturation magnetization of about 2000 gauss and no remnant magnetization. The particles could then be degraded back to the original 30 Angstrom magnetic particle by exposure to pH 6 acid for 24 hours.

Example 11: Formation of a Magnetic Cluster 10 grams of hydroxyl terminated particles as prepared in Example 7 and 10 grams of carboxy terminated magnetic particles as prepared in Example 9 were mixed. To the mixture was added 10 grams of 1 Normal HCl. The reaction mixture was heated to 60 degrees C. and stirred for a period of 24 hours. The resulting materials were ester linked magnetic particle clusters about 1 micron in diameter that had a saturation magnetization of about 2000 gauss and no remnant magnetization. The particles could then be degraded back to the original 20 Angstrom magnetic particle by exposure to pH 6 acid for 24 hours.

Example 12: Formation of a Magnetic Cluster-Polymer Bead 10 gm of 30 A particles were prepared as in Example 3. The particle slurry was mixed into an aqueous 25% 100 cc solution of polyvinyl alcohol (mw 50,000 daltons) and transferred into a 16 oz glass jar filled 25% with ¼" ss balls. The suspension was mixed on a ball mill for a period of 2 hours. When the mixing was completed, the slurry was removed from the jar mill and added to a blender filled with 500 cc of acetone. The mixture was agitated in the blender at the highest speed for 10 minutes causing the polymer to flocculate onto the magnetic particle's surface. The magnetic beads were collected. The resulting polymer encapsulated magnetic particle clusters were about 100 Angstroms to 2 microns in diameter and had a saturation magnetization of about 2,000 gauss and had no remnant magnetization. The bead could easily be degraded by dissolving it in hot water and the resulting unit crystals had no magnetization.

Example 13: Formation of a Magnetic Cluster-Polymer Bead 10 gm of 30 A particles were prepared as in Example 3. The particle slurry was mixed into a glass, 25% 100 cc solution of hydroxy propyl cellulose (mw 50,000 daltons) and transferred into a 16 oz glass jar filled 25% with ¼" ss balls. The suspension was mixed on a ball mill for a period of 2 hours. When the mixing was completed, the slurry was removed from the jar mill and added to a blender filled with 500 cc of acetone. The mixture was agitated in the blender at the highest speed for 10 minutes causing the polymer to flocculate onto the magnetic particle's surface. The magnetic beads were collected. The resulting polymer encapsulated magnetic particle clusters were about 100 Angstroms to 2 microns in diameter and had a saturation magnetization of about 2,000 gauss and had no remnant magnetization. The bead could easily be degraded by dissolving it in hot water and the resulting unit crystals had no magnetization.

Example 14: Formation of a Magnetic Cluster-Polymer Bead 10 gm of 30 A particles were prepared as in Example 3. The particle slurry was mixed into a glass, 25% 100 cc solution of carboxymethy cellulose (mw 50,000 daltons) and transferred into a 16 oz glass jar filled 25% with ¼" ss balls. The suspension was mixed on a ball mill for a period of 2 hours. When the mixing was completed, the slurry was removed from the jar mill and added to a blender filled with 500 cc of acetone. The mixture was agitated in the blender at the highest speed for 10 minutes causing the polymer to flocculate onto the magnetic particle's surface. The magnetic beads were collected. The resulting polymer encapsulated magnetic particle clusters were about 100 Angstroms to 2 microns in diameter and had a saturation magnetization of about 2,000 gauss and had no remnant magnetization. The bead could easily be degraded by dissolving it in hot water and the resulting unit crystals had no magnetization.

Example 15: Formation of a Magnetic Cluster-Polymer Bead 10 gm of 30 A particles were prepared as in Example 3. The particle slurry was mixed into a glass, 25% 100 cc solution of poly(vinyl pyrrolidone) (mw 50,000 daltons) and transferred into a 16 oz glass jar filled 25% with ¼" ss balls. The suspension was mixed on a ball mill for a period of 2 hours. When the mixing was completed, the slurry was removed from the jar mill and added to a blender filled with 500 cc of acetone. The mixture was agitated in the blender at the highest speed for 10 minutes causing the polymer to flocculate onto the magnetic particle's surface. The magnetic beads were collected. The resulting polymer encapsulated magnetic particle clusters were about 100 Angstroms to 2 microns in diameter and had a saturation magnetization of about 2,000 gauss and had no remnant magnetization. The bead could easily be degraded by dissolving it in hot water and the resulting unit crystals had no magnetization.

Example 16: Formation of a Magnetic Cluster-Polymer Bead 10 gms of 30 A particles were prepared as in Example 3. The particle slurry was washed 5× with acetone by magnetic filtration of the suspended particles after each successive wash and decanting the supermagnetic liquid. The particle slurry was then washed 3× in cyclohexanone using the same technique as the acetone washing procedure, and diluted to 50 cc with cyclohexanone after the final wash.

The suspension was added to 100 cc of a 20% solution of polyester polyurethane block co-polymer (BF Goodrich Estane 5719) dissolved in cyclohexanone and mixed in a blender.

The slurry was then added to 200 cc of acetone in a blender as described in Example 12 and mixed at high speed for 5 minutes causing the urethane to flocculate and collapse onto the particle's surface forming beads about 0.5–1 micron in diameter.

The resulting beads had a magnetization of about 2,000 gauss and no remnant magnetization.

The beads could easily be degraded to unit crystals by contact in organic solvent or by hydrolytic decomposition of the ester bonds in the back bone of the polymer by boiling the beads in water for 24 hours or by autoclaving an aqueous suspension of the beads for 90 minutes.

Example 17: Formation of a Magnetic Cluster-Polymer Bead 10 gms of 30 A particles were prepared as in Example 3. The particle slurry was washed 5× with acetone by magnetic filtration of the suspended particles after each successive wash and decanting the supermagnetic liquid. The particle slurry was then washed 3× in cyclohexonone using the same technique as the acetone washing procedure, and diluted to 50 cc with cyclohexonone after the final wash.

The suspension was added to 100 cc of a 20% solution of polystyrene dissolved in toluene and mixed in a blender using a laboratory paddle stirrer for this.

The slurry was then added to 200 cc of acetone in a blender as described in Example 12 and mixed at high speed for 5 minutes causing the polystyrene to flocculate and collapse onto the particle's surface forming beads about 0.5–1 micron in diameter.

The resulting beads had a magnetization of about 2,000 gauss and no remnant magnetization. The beads could easily be degraded to unit crystals by contact in organic solvent.

Example 18 Formation of a Magnetic Cluster-Polymer Bead 10 gms of 30 A particles were prepared as in Example 3. The particle slurry was washed 5× with acetone by magnetic filtration of the suspended particles after each successive wash and decanting the supermagnetic liquid. The particle slurry was then washed 3× in cyclohexanone using the same technique as the acetone washing procedure, and diluted to 50 cc with cyclohexaone after the final wash.

The suspension was added to 100 cc of a 20% solution of polyvinyl acetate) polyvinyl chloride (Union Carbide VAGH) dissolved in cyclohexanone and mixed in a blender using a laboratory paddle stirrer for this.

The slurry was then added to 200 cc of acetone in a blender as described in Example 12 and mixed at high speed for 5 minutes causing the urethane to flocculate and collapse onto the particle's surface forming beads about 0.5–1 micron in diameter.

The resulting beads had a magnetization of about 2,000 gauss and no remnant magnetization. The beads could easily be degraded to unit crystals by contact in organic solvent or by decomposition of the backbone of the polymer by boiling the beads in CMF for 24 hours.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A biodegradable magnetic microcluster which comprises: a cluster of metal or metal oxide particles encapsulated within a macromolecular species, said particles having an individual crystal diameter of 70 Angstroms or less characterized in that said particles are non-magnetic in the unclustered state and a sufficient number of particles are encapsulated within said macromolecular species to provide a magnetic microcluster characterized in that the magnetic microcluster is about 100 Angstroms to 2 microns in size.

2. The biodegradable magnetic microcluster of claim 1 having a saturation magnetization of about 2000 gauss, and no remnant magnetization.

3. The polymer encapsulated particle microcluster of claim 1 wherein the macromolecular species are selected from the group consisting of poly(vinyl alcohol), hydroxypropyl cellulose, carboxymethylcellulose, poly(vinyl pyrrolidone), polyurethanepolyester copolymers, polystyrene and poly(vinyl acetate)-poly(vinyl chloride) copolymers.

* * * * *